US008758576B2

(12) United States Patent
Escoffier et al.

(10) Patent No.: US 8,758,576 B2
(45) Date of Patent: Jun. 24, 2014

(54) DEVICE AND METHODS FOR COUPLING/UNCOUPLING A TARGET OR AN OBJECT PRESENT IN A SAMPLE

(75) Inventors: Celine Escoffier, Dijon (FR); Gilles Marchand, La Mure (FR); Frederic Revol-Cavalier, Seyssins (FR); Francoise Vinet, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 1512 days.

(21) Appl. No.: 10/555,099

(22) PCT Filed: May 17, 2004

(86) PCT No.: PCT/FR2004/050195
§ 371 (c)(1),
(2), (4) Date: Nov. 2, 2005

(87) PCT Pub. No.: WO2004/104580
PCT Pub. Date: Dec. 2, 2004

(65) Prior Publication Data
US 2007/0034511 A1     Feb. 15, 2007

(30) Foreign Application Priority Data

May 21, 2003    (FR) ...................................... 03 50166

(51) Int. Cl.
*C25D 17/00*         (2006.01)
(52) U.S. Cl.
USPC ...... 204/194; 204/403.01; 204/670; 204/671; 435/283.1; 435/287.1; 435/287.2
(58) Field of Classification Search
USPC ................... 435/283.1, 287.1, 287.2; 204/194
See application file for complete search history.

(56) References Cited

U.S. PATENT DOCUMENTS

| | | | | |
|---|---|---|---|---|
| 5,843,650 A | * | 12/1998 | Segev | 435/6 |
| 5,871,918 A | * | 2/1999 | Thorp et al. | 435/6 |
| 5,919,523 A | | 7/1999 | Sundberg et al. | |
| 6,113,768 A | | 9/2000 | Fuhr et al. | |
| 6,225,059 B1 | * | 5/2001 | Ackley et al. | 435/6 |
| 6,238,909 B1 | * | 5/2001 | Choong et al. | 435/287.2 |
| 6,280,595 B1 | | 8/2001 | Montgomery | |
| 6,395,489 B1 | | 5/2002 | Stanley | |
| 6,514,762 B1 | | 2/2003 | Wang | |
| 6,630,359 B1 | | 10/2003 | Caillat et al. | |
| 2004/0175708 A1 | * | 9/2004 | Caillat et al. | 435/6 |

FOREIGN PATENT DOCUMENTS

| | | |
|---|---|---|
| EP | 1 072 617 | 1/2001 |
| FR | 2 103 359 | 4/1972 |
| FR | 2 818 287 | 6/2002 |
| JP | 2000106874 | 4/2000 |
| WO | 99/29711 | 6/1999 |
| WO | WO 00/07728 | 2/2000 |
| WO | 02/051856 | 7/2002 |
| WO | 02/090963 | 11/2002 |
| WO | WO 02/088300 A1 | * 11/2002 |

OTHER PUBLICATIONS

Oxford English Dictionary. "Border", Second edition, 1989; online version Nov. 2010. <http://www.oed.com:80/Entry/21618>; accessed Jan. 27, 2011.*
Katz et al. "pH-switched electrochemistry of pyrroloquinoline quinone at Au electrodes modified by functionalized monolayers", Journal of Electroanalytical Chemistry, vol. 408, pp. 107-112 1996.
Yousaf et al. "Dynamic substrates: modulating the behaviors of attached cells", New Technologies for Life sciences: A trends guide, pp. 28-35 2000.
Chechik et al. "Reactions and Reactivity in Self-Assembled Monolayers", Advanced Materials, vol. 12, No. 16, pp. 1161-1171 2000.
Kaganer et al. "Surface Plasmon Resonance Characterization of Photoswitchable Antigen-Antibody Interactions", Langmuir, vol. 15, pp. 3920-3923 1999.
Yamato et al. "Novel patterned cell coculture utilizing thermally responsive grafted polymer surfaces", Journal of Biomedical Materials Research, vol. 55, No. 1, pp. 137-140 2001.
Revell et al. "Self-Assembled Carbohydrate Monolayers: Formation and Surface Selective Molecular Recognition", Langmuir, vol. 14, pp. 4517-4524 1998.
Spinke et al. "Molecular recognition at self-assembled monolayers: Optimization of surface functionalization", J. Chem. Phys., vol. 99, No. 9, pp. 7012-7019 1993.
Tidwell et al. "Endothelial Cell Growth and Protein Adsorption on Terminally Functionalized, Self-Assembled Monolayers of Alkanethiolates on Gold", Langmuir, vol. 13, pp. 3404-3413 1997.

(Continued)

*Primary Examiner* — Allison Ford
*Assistant Examiner* — Susan E Fernandez
(74) *Attorney, Agent, or Firm* — Oblon, Spivak, McClelland, Maier & Neustadt, L.L.P.

(57) ABSTRACT

The device of the invention comprises a support having a surface comprising an attachment zone (Z) capable of being functionalized with a probe (A) capable of binding, according to the pH and reversibly, to a target (B) so as to attach it; a working electrode (WE) and a counterelectrode (CE) for this working electrode, arranged on the support in the vicinity of the attachment zone; and means for applying a given electric current or a given potential to said working electrode so as to cause, when said attachment zone and said electrodes are immersed in an aqueous solution, a local variation in pH in the region of said attachment zone.

The method for attaching and/or detaching a target or an object according to the invention uses this device, the attachment and/or the detachment being electrochemically controlled with the working electrode.

13 Claims, 4 Drawing Sheets

(56) References Cited

OTHER PUBLICATIONS

Kaifer. "Functionalized Self-Assembled Monolayers Containing Preformed Binding Sites", Israel Journal of Chemistry, vol. 36, pp. 389-397 1996.

Piro et al. "A polyaminoquinone film for dopamine entrapment and delivery", Journal of Electroanalytical Chemistry, vol. 499, pp. 103-111 2001.

Wang et al. "On-demand electrochemical release of DNA from gold surfaces", Bioelectrochemistry, vol. 52, pp. 111-114 2000.

Voldman et al. "Microfabrication in Biology and Medicine", Annu. Rev. Biomed. Eng., vol. 1, pp. 401-425 1999.

Hofmann et al. "Fully Electronic DNA Detection on a CMOS Chip: Device and Process Issues", Electron Devices Meeting. IEDM '02. Digest. International, pp. 488-491 2002.

Godillot et al. "Direct chemical functionalization of as-grown electroactive polypyrrole film containing leaving groups", Synthetic Metals, vol. 83, pp. 117-123 1996.

Baeuerle et al. "Post-Polymerization Functionalization of Conducting Polymers: Novel Poly(alkylthiophene)s Substituted with Easily Replaceable Activated Ester Groups", Advanced Materials, vol. 8, No. 3, pp. 214-218 1996.

\* cited by examiner

DEVICE AND METHODS FOR COUPLING/UNCOUPLING A TARGET OR AN OBJECT PRESENT IN A SAMPLE

TECHNICAL FIELD

The present invention relates to a device and to methods for attaching or detaching a target or an object present in a sample to or from a probe attached to a support.

The target may, for example, be chosen from the group consisting of a chemical or biological molecule, a cell, a bacterium, a functionalized particle, such as a latex bead or a glass bead, a protein, a deoxyribonucleic acid (DNA or cDNA), an oligonucleotide, a ribonucleic acid, a peptide nucleic acid (PNA), an enzyme, a molecule to be transfected, an active principle, for example of pharmacological interest, etc. The probe may, for example, be a chemical or biological molecule or biological object capable of binding both to the support and to the target. The object may be one of the abovementioned elements, it is "carried" by the target.

The invention finds applications in a large number of fields, for example in methods for separating or purifying biological molecules or objects, in methods for concentrating biological molecules or objects, in detection methods, etc.

The invention applies to all microsystems that use the attachment and the detachment of biological and/or chemical targets or objects. It can in particular apply to microsystems for biology, for example to DNA chips, to cell-sorting chips; to chemical microsystems, for example activation of functionalization or detection chips; or combinatorial chemistry chips, for example targeting of active molecules.

PRIOR STATE OF THE ART

In the text below, the references between [ ] refer to the attached reference list.

Most of the current systems and techniques use processes other than electrochemistry. Typically, these techniques make use either of physical interactions such as electrostatic, hydrophilic/hydrophobic, steric, topographic, physisorption interactions, etc., or depend on a chemical process. Some systems make use of processes that can be described as "active" since an electrical, electrochemical or photochemical instruction is involved in the modulation of surface properties. In general, the combination of attachment/detachment of molecules by these systems is neither reversible nor controllable since the latter are often passive and/or non-specific.

Among the systems for attaching and detaching molecules to or from a surface that are suitable for biological and/or chemical applications, some use surface property modifications.

Mention may, for example, be made of the electrochemical alteration of an active group present on a surface, followed by chemical reaction: protonation/deprotonation of end acid and/or base groups of self-assembled layers of thiols, redox couples of $X^{(-)}/XH$ type, at the surface or in solution, so as to bring about deprotection. Such systems are described, for example, in references [1] and [2] cited in the appendix. In these systems, the redox couples used are relatively complex and the solvents used for the chemical synthesis are most commonly nonaqueous, which inevitably results in the spectrum of use being limited. It involves, for example, an electrochemical reduction or oxidation resulting in a chemical reaction, for example reduction of a quinine to a hydroquinone followed by lactonization (detachment of ligands or of cells) or else oxidation of a hydroquinone to a quinine followed by a Diels-Alder reaction (immobilization of ligands or of cells) as is described in reference [2].

These techniques, that are partly electrochemical, do not unfortunately make it possible to provide reversible attachment since they are coupled to an irreversible chemical reaction: synthetic chemistry as shown in reference document [3].

Mention may also be made of systems that use the photochemical activation of a group present on a surface, such as those described in references [2] and [4]. These systems use a conformational change of the group by isomerization induced by photons, and a reaction with, or a recognition by, the photoactivated product, such as an enzyme, an antibody, a ligand or chemical groups [5].

The attachment of objects, in this case, can unfortunately result in a non-specific attachment [2] and requires an optical bench and an activation system that is complex and tricky to use.

Mention may also be made of techniques that use a change in hydrophilic/hydrophobic behaviour of a surface coated with specific polymers ("LCST": "Lower Critical Solution Temperature") as described in document [6]. These polymers pass from one state to the other if their temperature is above or below a critical temperature (around 37° C.). This makes it possible, by hydrophilic/hydrophobic attraction/repulsion, to attach or detach objects (having hydrophilic or hydrophobic properties) by cooling (or heating).

However, for large objects on a microsystem scale, for example cells, the detachment is accompanied by a considerable reaction inertia. In addition, the integration of these polymers into a microsystem requires a great deal of additional research and adaptation effort in terms of microtechnology processes [7].

Mention may also be made of systems that use the functionalization of a surface with groups that may effect a chemical and/or steric recognition with another group present on the object to be anchored [8], [9] and [10]. These systems immobilize chemical or biological functions such as acid, carboxyl, amine, hydroxyl groups, etc., or oligonucleotides, by means of self-assembled monolayers ("SAMs") of thiols that have been functionalized, by means of silanization or by means of functionalized conducting polymers, or by means of grafting of organometallic complexes or else of cage molecules [11].

Unfortunately, in these systems, the attachment and detachment can be neither controlled nor carried out locally. These systems therefore lack precision.

Mention may also be made of systems that use an electrical, electrostatic action, as described in reference [12]. These systems use, for example, an electric field to separate two parts of a molecular assembly bearing charges [13], cathode desorption (electrostatic repulsion) [14] or attachment or detachment of charged objects to maintain the electroneutrality of the zone of attachment or detachment or inside a membrane (volume).

These techniques do not, however, provide any real specificity and any object bearing a charge will be simultaneously attracted/repulsed. The reversibility of this approach with respect to complex objects of considerable volume on a microsystem scale, for example a cell or a bacterium, is not acquired. In the case of maintaining the electroneutrality of a membrane, the size of the objects that can be immobilized is a limiting factor.

There is therefore a real need for a system that does not have the numerous problems of the abovementioned systems of the prior art.

DISCLOSURE OF THE INVENTION

The system of the present invention, in the form of a device and of methods using this device, makes it possible as a matter of fact to provide a solution to these many problems of the prior art. In particular, it uses aqueous solutions, it can be reversible, specific, precise, reproducible, simple to use, it makes it possible to adapt both to the attachment of large targets or objects such as cells and to small targets or objects such as chemical molecules, it can be readily adapted to microtechnological methods, and it allows a local control and implementation. In addition, the activation of the device for the attachment/detachment has a low reaction inertia.

In the subsequent description, the term "target" will be reserved for molecules or objects that bind directly to the probe so as to form a probe-target bond. The term "object" will be reserved for molecules or objects that are attached to the probe by means of the "target", forming with said target an object-target bond. In other words, the object does not bind directly to the probe, but by means of the target that is recognized by the probe.

The attached FIGS. 1 and 2 represent diagrammatically a device according to the invention.

The device of the present invention is a device that allows the localized attachment or detachment of a target (B) to or from a probe (A) attached to a support.

It comprises:
- a support having a surface comprising an attachment zone (Z) capable of being functionalized with a probe (A) capable of binding to a target (B) so as to attach it;
- a working electrode (WE) and a counterelectrode (CE) for this working electrode, placed on the support in the vicinity of the attachment zone; and
- means for applying a given electric current or a given potential to said working electrode so as to cause, when said attachment zone and said electrodes are immersed in an aqueous solution, a local variation in pH in the region of said attachment zone.

The method of the invention is, according to a first embodiment, a method for attaching a target (B) present in an aqueous sample to a probe (A), said method comprising the following steps:

a) bringing the aqueous sample into contact with the attachment zone of a device according to the invention, said attachment zone being functionalized with the probe (A) capable of binding, according to the pH, to the target (B) so as to attach it;

b) applying an electric current or a potential to the working electrode of said device so as to locally modify, in the region of said attachment zone, the pH of the aqueous sample such that the probe recognizes and binds specifically to the target so as to attach it.

The method of the invention is, according to a second embodiment, a method for attaching and detaching a target (B) present in an aqueous sample to and from a probe (A), said method comprising the following steps:

a') bringing the aqueous sample comprising the target (B) into contact with the attachment zone of a device according to the present invention, said attachment zone being functionalized with the probe (A), such that the target (B) attaches to said probe;

b') applying an electric current or a potential to the working electrode of said device so as to locally modify, in the region of said attachment zone, the pH of the working solution such that the target (B) detaches from the probe (A).

The aqueous sample is an aqueous solution comprising the target to be attached to the probe. It originates, for example, from a simple mixture of the target with an aqueous solution, or from a sample taken from an animal or a plant, from a culture medium, from a biological culture reactor (cell culture, yeast, fungi, algae, enzymes, etc.), from a chemical reactor, from a gas (for example, ambient air) or from a liquid or gaseous industrial effluent. If this sample does not allow the method of the invention to be carried out, for example because of its nature (gas, solid), its concentration or the elements that it contains (solid residues, waste, suspension, interfering molecules, etc.), the method of the invention also comprises a prior step consisting in dissolving the sample in an aqueous solution by means of the techniques known to those skilled in the art. The essential point is that the sample to which the method of the invention is applied is aqueous.

In fact, in the present invention, the water present in the sample can undergo either an oxidation or a reduction according to the electrochemical conditions (current or potential) applied to the working electrode. The couples involved, $O_2/H_2O$ and $H_2O/H_2$, have respective potentials determined by $E_1=1.23-0.06$ pH, and $E_2=-0.06$ pH. The initial pH of the working solution, and also the kinetic immunity of the reactions, dependent on the electrolyte and on the electrodes used, determines the working potential that makes it possible to obtain the desired variation in pH. The kinetic immunity range is the potential range greater than the theoretical potential (given by the above equations) in which no reaction takes place, contrary to that theoretically predicted. It is therefore necessary to apply an overpotential in order to overcome the kinetic immunity. For example, on a platinum electrode, the cathodic overpotential is $-0.2$ V and the anodic overpotential 0.6 V.

In the present invention, the attachment process involves the formation of a chemical bridge between the probe and its target: either via a local variation in pH by means of the device of the invention, the medium in the vicinity of the attachment zone being made locally acidic or basic by electrochemical activation according to the first embodiment of the invention ("active attachment"); or spontaneously, for example due to the pH of the working aqueous solution, due to a chemical or biological affinity between the probe and the target, due to a steric recognition, etc., during the bringing into contact of the probe and target according to the second embodiment of the invention ("passive attachment"). The formation of this chemical bridge takes place between two groups, one of which belongs to the probe immobilized at the surface of the attachment zone, and the other to the target.

Thus, according to the choice of the embodiment of the invention, when the target is present in the sample, it is attached via the probe to the attachment zone either by means of the local variation in pH induced in the region of said attachment zone by the electrochemical microcell, or spontaneously.

In the first embodiment of the invention, and when the probe-target binding is reversible, for example according to pH, the target can be released from the probe, for example by applying a step consisting in interrupting the application of the electric current or of the potential to the working electrode or in applying a different electric current or potential to said working electrode so as to locally modify the pH of the working solution or of a rinsing solution so that the target detaches from the probe. In this case, the method of the invention therefore comprises an attachment and an "active" detachment of the target. For example, it is possible to apply to the working electrode a current or a potential that makes it possible to return to the initial pH value or to a value that allows release of the target.

In the first embodiment of the invention, and when the probe/target binding is reversible, the target may also be released using a rinsing solution that breaks the probe-target binding, for example due to the pH or to the chemical nature of this rinsing solution.

One or more steps consisting in rinsing the attachment zone, before and/or after step b), may also be carried out, for example for the purposes of purification of the target attached to the probe. The rinsing solution is then, of course, preferably a solution that preserves the probe-target binding. This solution may, for example, be identical to the aqueous solution that has enabled the preparation of the sample.

According to a variant of the second embodiment, the attachment of the target by the probe in step a') can be carried out by application of an electric current or of a potential to the working electrode of said device so as to locally modify, in the region of said attachment zone, the pH of the working solution such that the target (B) attaches to said probe (A). In this case, the attachment and the detachment of the target are referred to as "active". According to this variant, the attachment can be carried out according to the first embodiment of the invention, and the detachment can be carried out according to the second embodiment of the invention.

The abovementioned documents of the prior art show that a purely electrochemical approach in accordance with the present invention, i.e. without coupling with another type of irreversible reaction, has never been dealt with in the techniques of the prior art with the aim of controlling and varying the properties of attachment and/or detachment of a target to or from a surface functionalized with a probe, for example of a microsystem.

The device may advantageously be in the form of a microsystem comprising one or more device(s) according to the invention. Each device forms a real electrochemical microcell comprising at least two electrodes: a working electrode and a counterelectrode; and, optionally, a reference electrode (RE); and also an attachment and/or detachment zone. The latter can itself also be an electrode, for example when its functionalization with the probe is carried out electrically or electrochemically, for example by electrografting.

According to the invention, an electrochemical microcell for an attachment and/or detachment zone is preferable in order to obtain good localization of the variation in pH, and therefore a well-localized attachment of the targets. Thus, the device of the invention makes it possible to carry out a method of localized attachment and/or detachment in which it is possible to choose specifically, precisely, and independently of one another, the zone(s) where a target is to be attached or detached, from a matrix of several potential attachment and/or detachment zones distributed at the surface of a microsystem and functionalized with one or more identical or different probes.

The support on which the device of the present invention can be fabricated can be any support that allows the present invention to be implemented. It may, for example, be a biochip support such as those conventionally used, for example made of silicon, glass, polymer, metal, plastic, etc. Supports that can be used in the present invention are described, for example, in the documents referenced [15] and [16] in the reference list.

The attachment and/or detachment zone can advantageously consist of a conductive material if an electrical or electrochemical functionalization is necessary. It may consist of any other material that can be used to graft the probe if other functionalization techniques are chosen, for example chemical functionalization techniques. It may be a material that has been chemically or biologically modified so that the probe can be attached thereto. It may be the actual surface of the support or a coating, deposited onto this support by the usual depositing techniques known to those skilled in the art, allowing functionalization with the probe. This coating may, for example, be Si, glass, $SiO_2$ (allowing silanization), an appropriate conductive polymer or copolymer, such as those used to fabricate biochips, in particular for the attachment of molecular probes of biochips, for example polypyrrole, a metal, such as Au, Ag, or Pt, for example in order to perform electrografting, for the formation of self-assembled monolayers, etc. The attachment zone may be delimited, for example, by the localization of the probes that functionalize it, and by the vicinity of the electrodes.

The device of the present invention may be provided, for example for commercialization purposes, as a substrate comprising a non-functionalized attachment zone and the electrodes. The user of this device can then readily, by means of conventional techniques for functionalizing a biochip surface, functionalize this zone with a probe that he or she has chosen according to the target that he or she wishes to attach in order to obtain a device that makes it possible to carry out one of the methods of the invention.

The device of the present invention can also be provided, for commercialization purposes, in a form already comprising its attachment zone functionalized with a probe (A) capable of binding, according to the pH, to the target (B) so as to attach it. It then makes it possible to carry out one of the methods of the invention immediately, without prior functionalization of the attachment/detachment zone, for the target corresponding to said probe.

In general, the functionalization of the attachment zone with the probe, which consists in immobilizing the probe on the attachment zone, can be carried out by means of the usual techniques of chemical or electrochemical grafting ("electrografting"), for example such as those described in the documents referenced [8] to [12] and [17] and [18] in the attached reference list.

The attached FIGS. 1 and 2 represent an attachment zone (Z) functionalized with a probe "A", for example a biological or chemical probe.

The probe is generally chosen according to the target. The probe "A" and the target "B" (see FIGS. 1 and 2) are composed of one or more elements preferably having pH-stable bonds and possessing chemical groups that can interact and attach in the presence of an acidic or basic pH during the electrochemical attachment. For example, the probe "A" may carry one (or more) electrophilic group(s) that can react, in an acidic or basic medium, with one (or more) nucleophilic group(s) carried by the target "B", and vice versa. The binding between the probe "A" and the target "B" may also consist of the formation of a disulphide bridge or disulphide bridges by acidification of the medium according to the reaction

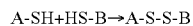

A-SH+HS-B→A-S-S-B

Thus, according to the invention, the probe can be chosen, for example, such that it is capable of binding to the target so as to attach it by means of an electrophilic group, for example chosen from aldehyde, halide, thiocyanate, isocyanate, activated ester, carbamate, epoxide, etc., functions.

The probe can also be chosen such that it is capable of binding to the target so as to attach it by means of a nucleophilic group, for example chosen from amine, alkoxide, phenol, phenate, oxyamine, hydrazine, etc., functions. According to the invention, the probe can be chosen, for example, such that it can form, in the working solution, with the target molecule so as to attach it, a bond chosen from a hydrogen, peptide, amide, sulphonamide, carboxylic acid ester, sulphonic acid ester or substituted silanoate bond.

In general, according to the invention, the probe can be chosen from a deoxyribonucleic acid (DNA or cDNA), an oligonucleotide, a ribonucleic acid, a peptide nucleic acid (PNA), a protein, an enzyme, an enzyme substrate, a hormone receptor, a hormone, an antibody, an antigen, a eukaryotic or prokaryotic cell or fragments of such cells, an alga, a microscopic fungus, etc. The choice is made according to the target. For example, in the abovementioned group, the target may be an oligonucleotide complementary to the probe oligonucleotide, an enzyme substrate, an antibody specific for an antigen, etc.

The localization of the attachment of the target to the probe of the attachment zone can be determined by a specific attachment when the probe-target assembly has a unique complementarity. It may, for example, be a probe-target attachment that exploits the sequence complementarity of two oligonucleotide strands, for example of RNA or of DNA, one of these two strands being attached to the support so to form the functionalized attachment zone, the other strand constituting the target to be attached. The binding between the probe and the target then takes place in the form of pairing of the complementary bases of the two strands. It may involve pairs of biological molecules other than oligonucleotides complementary to one another, that are known to those skilled in the art and involve pH-sensitive binding, for example chosen from the abovementioned list, for example substrate/enzyme, antibody/antigen, hormone/receptor, etc. This possibility of specific attachment advantageously makes it possible to precisely choose the point of the attachment for a given object.

According to a variant of the abovementioned two embodiments of the present invention, also represented in FIG. 1, the target "B" can be used to carry an object "C", for example an object to be attached and/or detached which must be extracted from a sample, an object to be isolated, an object to be detached with a time delay, etc.

This object can be attached to the target "B" prior to, simultaneously with, or subsequent to the assembly of "A"+"B". If B carries an object "C", the latter is then attached and/or detached by means of "B" to or from A. No other electrically generated phenomenon, such as the electric field, is involved in the attachment via the electrochemical process of the object "C" for example to the surface of a microsystem.

Thus, according to the invention, in one or other of the embodiments, the method can also comprise the following step: (x) attachment of an object to the target.

This variant has in particular the advantage that, for a given probe/target couple, for example for which the attachment/detachment conditions according to the invention are well known and controlled, for example a probe/target couple in the form of complementary oligonucleotide strands or in one of the forms presented in the examples below, it is possible to attach/detach any one of the abovementioned objects according to the method of the invention, provided that a bond can be formed between the object and the target, and that this target/object couple can be attached/detached to/from the probe by means of the method of the invention that is carried out.

This variant also has the advantage that, when an object must be attached/detached according to the method of the invention, and when it is not chemically possible to establish a direct electrochemical interaction between the object and the probe (the object would then be a target for the purpose of the present invention), the object is in a way "carried" by the target, and it is the latter that interacts with the probe so as to attach to or detach from the attachment zone. It is then sufficient to attach the object to the target by means of any one of the methods known to those skilled in the art.

Preferably, the object "C" having been determined, a probe-target couple for which the recognition and the binding will not be impaired and/or prevented by the attachment of the object "C" to the target will be chosen. Conversely, for a given probe-target couple, the object "C" will be chosen such that its attachment to the target does not impair and/or prevent the probe-target binding.

The object "C" may, for example, be chosen from the group consisting of a molecule, a cell; a bacterium; functionalized beads, for example latex beads, glass beads, etc.; a protein; an enzyme; an antibody, for example in order to recognize and immobilize a cell; a biological fragment; molecules to be transfected; molecules of biological interest; active principles; molecules of pharmacological interest; chemical groups, etc. The object "C" can also be a molecule or an object such as the target "B".

By way of illustration, the object "C" may be a label intended to demonstrate the probe-target binding. It may for example be any one of the labels known to those skilled in the art and used to demonstrate chemical or biological molecules or molecular recognition reactions between a probe and its target on a biochip. It may, for example, be a fluorescent molecule, an electroactive molecule, etc. An example of such an assembly is given below.

In the abovementioned step consisting in attaching an object to the target, since the object is a label, the method of the invention may also comprise a step consisting in detecting the labelled target. Since the abovementioned labels are known, it is not necessary to recall here the techniques known to those skilled in the art for detecting a label.

In the methods of the present invention, the probe may also carry a molecule such as a label, for example in order to demonstrate the probe-target binding, provided that this molecule does not impair said binding. This molecule may be attached to the probe by the usual chemistry techniques, before or after functionalization of the attachment zone with the probe. For example, when this molecule is a label, it can be chosen from a chemical molecule (for example dioxigenin), a fluorophore (for example fluorescein, a "molecular beacon" and its fluorescent label), an electrochemically active molecule (for example ferrocene), a biologically active molecule (for example an enzyme), a radioactive label (for example containing one or more isotope(s) of phosphorus [P32]). In another embodiment of the present invention, a biotin may, for example, be attached to the probe (the probe carries a biotin), and the target may be labelled with streptavidin-phycoerythrin.

According to the invention, the attachment of the target "B" by the probe "A" can be preceded by an electrochemical activation of the probe, by application of one or more electrochemical potential(s) or current(s) to the working electrode. This activation makes it possible to effect a local variation in pH (acidification or basification), limited to the vicinity of the working electrode (active electrode) and of the attachment zone. The application of one or more suitable electrochemical potential(s) or current(s) causes an electrochemical reaction, the products of which result, for example, in an instantaneous and localized hydroxylation or protonation of the solution in contact with the microsystem, and thus the formation of the bond between the probe and the target, and the attachment of the latter, by the probe, to the attachment zone. For example, the electrophilic groups and the nucleophilic groups of the probe and of the target interact and attach according to A+B→A-B.

The electrochemical activation can be carried out in the solution(s) used for the assembly, for example "A"+"B-C" or "A"+"B"+"C" or "A-B"+"C", and therefore does not require rinsing of the system, or in any other "post-assembly" solution if the latter is at least partly aqueous, preferably saline, and even more preferably buffered, provided that the bonds involved are not prevented in the implementation of the method of the invention.

The process of detachment, via the electrochemical process, of the target B, or B-C if an object "C" is attached to the target, involves, firstly, a reversible attachment between the probe "A" and the target "B" by means of attachment bridge comprising pH-sensitive groups as described above and, secondly, a cleavage of this bridge, carried out locally (at the site to be detached), subsequent to a local and reversible variation in pH. This detachment process is represented diagrammatically in FIG. 2.

The application of one or more suitable electrochemical potential(s) or current(s) causes an electrochemical reaction, the products of which lead for example to an instantaneous and localized hydroxylation or protonation of the solution in contact with the microsystem, and thus the breaking of the binding between the probe and the target. During the detachment step, under the influence of the electrochemical variation in pH, the groups sensitive to this variation (for example, hydrogen, peptide, amide, sulphonamide, carboxylic acid ester, sulphonic acid ester, substituted silanoate bonds) separate according to A-B→A+B. This reversible and localized cleavage of the attachment bridge can also bring about the detachment of the object "C", if it is present, which then goes back into solution in the form B-C or B+C. The detachment of C depends of course on the chemical nature of the bond that binds it to B.

The application of one or more suitable electrochemical potential(s) or current(s) brings about an electrochemical reaction, the products of which result in an instantaneous and localized hydroxylation or protonation of the solution in contact with the attachment zone, for example of the microsystem (assembly or post-assembly solution), which, according to the groups involved in the probe-target binding, results in the detachment of the target by the probe.

No other electrically generated phenomenon, such as electric field, is involved in the surface modulation (i.e. attached or detached state) via the electrochemical process. This is one of the many advantages of the present invention.

Consecutive attachments and detachments on the same surface, carried out by the inventors, have shown that the methods of the invention are reproducible. In fact, the methods of attachment and/or detachment are not definitive. For example, because of the existence of a reversible bond, such as those mentioned above, in the assembly bridge "A-B", the attachment and the detachment can be repeated, without impairment of the properties of the surface of the microsystem, as is shown in the examples below. This is one of the many advantages of the present invention.

In the device of the present invention, the working electrodes and counterelectrode can, as is usual for these elements, in particular in the microsystems known to those skilled in the art, consist of a conductive material, and preferably of a noble metal, or an alloy of a noble metal, for example Au, Pt, Pd, or Ir; or a semiconductive material, for example doped or carbonized silicon, suitable for electrochemistry, in the range of potentials used. It may be a conductive polymer, a conductive adhesive, polypyrrole, etc.

They may be placed in the vicinity of the attachment zone using the usual microelectronics techniques for placing electrodes on microsystems such as biochips. This may involve, for example, vacuum techniques for depositing metals, for example plasma-enhanced chemical vapour deposition (PECVD) or sputtering, etc. Techniques that can be used in the present invention are described in documents [19] and [20] of the attached reference list.

The attachment zone, in particular if it requires a particular treatment, for example for the attachment of the probe, can be placed in the vicinity of the electrodes after they have been produced. It can also be placed on the surface of the support before they have been produced.

The attached FIGS. 3 and 5 are examples of arrangements of the electrodes and of the attachment zone that can be used to constitute the device of the present invention. Of course, other arrangements can also be used in the context of the invention, based on the information hereby provided.

According to the invention, the working electrode preferably borders or surrounds the attachment zone. More preferably, the working electrode borders or surrounds the attachment zone and the counterelectrode borders or surrounds said working electrode. According to the invention, the working electrode, the counterelectrode and the attachment zone are advantageously in a design chosen from an interdigitated comb design, a spiral design or a concentric design (see, for example, attached FIGS. 3 and 5). This is because these designs are favourable to the application of the methods of the invention.

The attachment and/or detachment zone is preferably located as close as possible to the electrode used for the electrochemical activation (working electrode) and preferably coplanar with said electrode so as to ensure a better electrochemical action.

The diagrams in FIGS. 1 and 2 have been drawn with a non-coplanar structure in order to distinguish more clearly the various elements of the device represented. In FIG. 3, the elements are coplanar. The position of the counterelectrode may or may not be coplanar with the attachment and/or detachment zone.

A reference electrode (RE) can also be attached to the device, placed so as to be able to measure the potential applied to the working electrode. For reasons of miniaturization, the reference electrode may be integrated into the microsystem. It may, for example, be an Ag/AgCl electrode or any other reference electrode known to those skilled in the art that can be used in the device of the present invention. Represented in the attached FIGS. 3 and 5 are possible arrangements of the reference electrode on devices in accordance with the present invention.

By way of example, the dimensions, in the plane of representation in these figures, of the electrodes and components used to obtain the devices of the invention may be as follows for a microsystem intended for a biochip application:

attachment zone (Z): diameter 1 to 1000 µm;
space between the attachment zone (Z) and the working electrode (WE), and between the working electrode and the counterelectrode (CE): space of 10 to 200 µm;
width of the working electrodes (Z) and counterelectrode (CE): 10 to 50 µm; and
the reference electrode (RE) is a parallelepiped of 10×500 µm.

These dimensions are in fact only limited by the limits of the dimensions that can be achieved in microelectronics with the current techniques.

Those skilled in the art can, of course, readily fabricate devices with other dimensions on the basis of the information hereby given and of their general knowledge.

The means for applying a given electric current or potential to the working electrode are those normally used for microsystems, in particular for electrochemical cells. They may comprise means of connecting the electrodes of the device to the source of electricity for applying the electric current to the working electrode. They may also comprise controlling means and measuring means in order to be able to regulate and monitor the potential applied to the working electrode.

The electrochemical potential(s) to be applied to the working electrode in order to perform the attachment and/or detachment depend(s) on the type of assembly bridge between the probe and the target ("A-B"), on the aqueous electrolyte solution in contact with the microsystem (working solution), and on the design and the material of the electrodes used.

According to the invention, the current can be applied to the working electrode continuously or discontinuously, in an increasing or decreasing manner, etc. This application depends in particular on the local variation in pH that the user wishes to induce. According to the invention, this or these potential or potentials or this or these current or currents may be cathodic, anodic or both.

The electric current can advantageously be applied in the form of potential trains. In fact, the inventors have demonstrated that a potential train advantageously makes it possible to localize the variation in the pH more successfully, but also to render it reversible. In this case, the means for applying a given electric current or a given potential to said working electrode advantageously comprise means for applying one or more given current or potential train(s) for one or more given period(s) of time.

This potential train or current train is preferably composed of a minimum of one signal (pulse, voltage ramp, etc.). The electrochemical current train or potential train applied can, for example, be chosen so as to cause a variation in pH and to immediately compensate for the latter, without any modification of the remainder of the environment taking place.

In general, the values of the electrochemical potential(s) used depend on the desired local variation in pH, and therefore on the nature of the probe-target bond in question. In general, given the type of reversible probe-target bonds towards which the present invention is directed, the potential values are preferably, without being limited thereto, from −3.0 V to +4.0 V (relative to an Ag/AgCl reference electrode) and preferably from −1.8 V to −0.8 V or between +1.2 to +2.2 V (relative to an Ag/AgCl reference electrode). The values of the currents used are those that make it possible to obtain the above potential windows by potentiometry.

The potential or the potential train or current train, according to the choice of application of the current, is preferably imposed for a sufficient period of time, ranging for example from 0.001 s to 58 000 s, or from 0.001 s to 20 000 s, in order to produce the variation in pH that allows attachment of the target or its detachment according to the method applied.

Each element of the potential train or current train has a time period, a value and a form that are specific to it, and that are independent of the other elements of the potential train.

For implementing the methods of the invention, the functionalized attachment zone and the electrodes are immersed by the aqueous sample. The sample volume is not determining since the variation in pH is precisely located in the region of the attachment zone. This sample is obtained by mixing a specimen (as defined above), or quite simply the target, with an aqueous solution. Buffered aqueous solutions are preferred for the preparation of the sample, but are not essential to the implementation of the methods of the invention. In fact, water is sufficient for the electrochemical activation.

The buffer advantageously makes it possible to limit the diffusion of the products of the electrochemical reaction ($OH^-$ or $H^+$) in the remainder of the solution, and improves the flow of these products in the vicinity of the working electrode and of the attachment/detachment zone. It allows a better localization of the variation in pH, promoting localization of the phenomena of attachment and detachment in the region of the attachment zone and of the working electrode. This aqueous solution may, for example, be a phosphate buffer solution, such as a solution of $Na_2HPO_4$, of $NaH_2PO_4$, of $KH_2PO_4$, etc., or a solution of a mixture of these buffers. The concentrations are generally between 0.001 mM and 10M, preferably between 1 mM and 1M.

Preferably, the aqueous solution is a saline solution. This is because this type of solution improves the electrical conduction and, for example, in the case of biological molecules (for example, proteins in general), it makes it possible to maintain the biological molecules in their active form (protein folding) and/or allows the probe/target binding, for the implementation of the method of the invention. When the probe and/or the target are biological molecules, the saline solution makes it possible to carry out the method of the invention in an aqueous solution that has an appropriate ionic strength.

More preferably, this solution is saline and buffered.

In general, the choice of this solution can be made in particular according to the nature of the probe and of the target, in particular this solution should preserve the chemical functions and the structure of the probe and of the target and should also allow the probe to attach to the target. In addition, it facilitates the implementation of the electrochemical method of the present invention by constituting an appropriate electrolyte medium.

According to the invention, the localization of the attachment and/or of the detachment of the target can therefore be controlled in particular through the choice:

- of the electrochemical device: the specific arrangements of the electrodes at the surface of the microsystem allow the localization of the variation in pH;
- of applying a current or a potential, as chosen, to one or more given cell(s) only, in the case of a matrix or of a set of electrochemical microcells according to the invention distributed over the surface of a support: in this case also, the variation in pH is localized at the place where the operator wishes it to be;
- of the solution in contact with the microsystem: the use of buffered saline solutions is preferable; and
- of an appropriate electrochemical method: for example, the inventors have noted that the application of electrochemical potential trains makes it possible to control the variation in pH more successfully.

The present invention finds a large number of applications, and a few examples only are mentioned here.

The present invention can apply in particular to methods of separating and recovering biological and/or chemical objects: for example, cell sorting by selective attachment, for example via an antibody specific for this type of cell, to the surface of the microsystem and then detachment in another solution and/or towards another part of the microsystem in order to perform other tasks, such as an analysis, a detection, etc.

The present invention can also apply to operations consisting in concentrating biological and/or chemical objects: for example, attachment of the objects present in a solution circulating above the attachment surface and then detachment in another solution that has a smaller volume, so as to facilitate the performing of other tasks such as an analysis, a detection, etc.

The present invention can also apply to the performing of biological and/or chemical reactions that require a time delay, for example: chemical deprotection, screening of molecules of pharmacological interest, etc.

The present invention can also apply to fundamental studies relating to the physicochemical, thermal, physical, surface or chemical properties, or to the change in functionality of objects, before, during or after attachment, for example: energy study of the mechanisms of cell attachment.

Thus, the device of the invention can be used, for example, in a method intended to purify or extract a target "B" or an object "C" attached to a target "B-C"; to concentrate a target "B" or an object "C" attached to a target "B-C"; to screen targets or objects attached to a target or to detect a target "B" or an object attached to a target "B-C". The target "B" and the object "C" have been defined above.

The present invention also finds, for example, an application in a method for purifying a target "B" or an object "C", said purification method comprising, for example, the implementation of the method of "active" or "passive" attachment according to the invention, with said target "B" or said object "C" bound to a target (said object being bound to said target before or after the attachment of the target by the probe) ("B-C") using an appropriate device according to the invention; rinsing of said attachment zone by means of said aqueous solution of by means of another solution that preserves the probe-target ("A-B") or probe-target-object ("A-B-C") binding; detachment of the object "B" or target-object ("B-C") either by interrupting the application of the electric current to the working electrode, or by applying a different electric current or a different potential in the region of said attachment zone so as to locally modify the pH of the working solution so that the target or target-object detaches from the probe, or by rinsing the device by means of an appropriate solution for detaching the target; and, optionally, rinsing the attachment zone so as to recover the target or target-object detached. The target "B" and the object "C" have been defined above.

This method also makes it possible to concentrate a target "B" or an object bound to a target "B-C", for example by using, in the abovementioned purification method, a volume for rinsing the target or the target-object detached that is smaller than the initial volume of the sample. The target "B" and the object "C" have been defined above.

The present invention therefore finds a very large number of applications for the fabrication of novel generations of biochips, or "lab-on-chip". These are, for example, microsystems comprising various working steps, carried out in one or more compartments, consecutively. The attachment or detachment operations can be used as a part of one or more of these steps, or as a step in its own right. The attachment and/or the detachment could make it possible to carry out various types of operations, such as:

operations consisting in separating and recovering biological and/or chemical objects: it is possible to imagine cell sorting by selective attachment, for example via an antibody specific for this type of cell, to the surface of the microsystem and then detachment in another solution and/or towards another part of the microsystem in order to perform other tasks (analysis, detection, etc.);

operations consisting in concentrating biological and/or chemical objects: for example, attachment of the objects present in a solution circulating above the attachment surface and then detachment in another solution that has a smaller volume, so as to facilitate the performing of other tasks, for example analysis, detection, etc.;

the performing of biological and/or chemical reactions that require a time delay, for example for screening of molecules of pharmacological interest, chemical deprotection, etc.;

fundamental studies relating to the physicochemical, thermal, physical, surface or chemical properties, or to the changing functionality of objects, before, during or after attachment, for example energy studies of the mechanisms of cell attachment.

Other characteristics, advantages and potential applications will further emerge on reading the examples that follow, given by way of illustration with reference to the attached figures.

EXAMPLES

Example 1

Fabrication of a Device According to the Invention

In this example, the device of the invention is fabricated on a silica support according to the protocol disclosed in document [15] in the attached reference list. The fabrication of the device comprises the following steps:

On a silicon substrate:
- oxidation of the surface of the substrate over a thickness of 1 µm;
- deposition of a metal layer (Pt or Au) on a Ti tie layer by means of an evaporation technique;
- structurization of the electrodes by photolithography and dry etching;
- passivation of the tracks by deposition of silicon oxide followed by formation of an aperture (photolithography then etching of the oxide) in the measurement electrodes;
- electrochemical deposition of silver onto the reference electrodes; and
- study of the chemical chlorination of the electrodes.

The fabricated devices are then connected to a potentiostat (AutoLab PGstat 100 from the company Ecochemie) so as to be able to measure and control the potential and/or the current applied. The design used is a conventional design for electrochemical cells, i.e. a three-electrode design: a working electrode, a counterelectrode and a reference electrode, the latter being optional.

Example 2

Example of Designs of Devices According to the Invention (Electrochemical Microcells)

Various electrochemical microsystems, the design of which is suitable for the attachment and the detachment, via the electrochemical process, according to the invention, were produced according to the protocol of Example 1.

Figure 5:
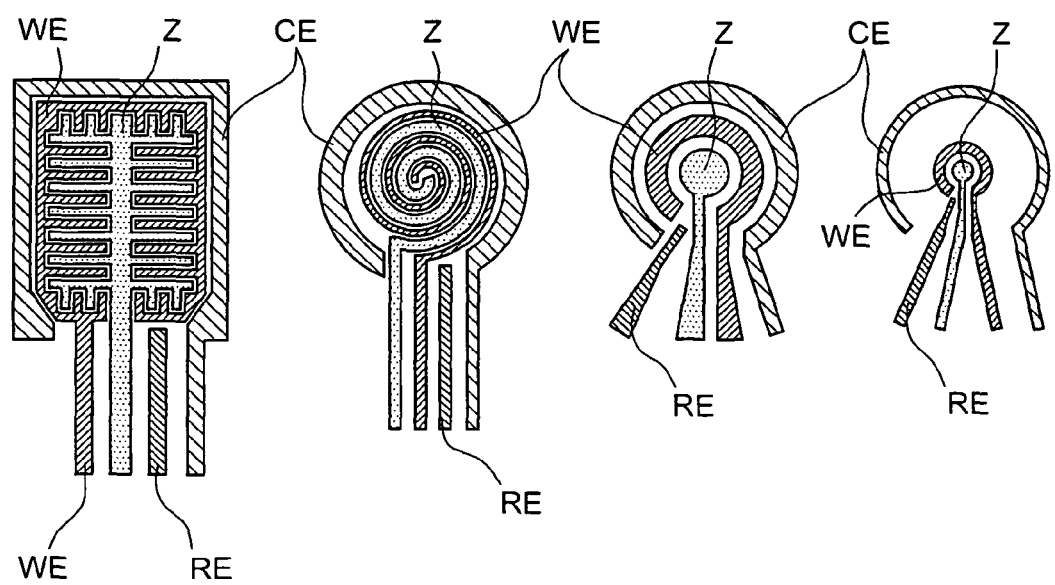
FIG. 5 represents, diagrammatically, examples of designs of devices in accordance with the present invention, comprising: an attachment zone (Z), a working electrode (WE), a counterelectrode (CE) and a reference electrode (RE) respectively, from left to right: in interdigitated, spiral and concentric form, constituting electrochemical microcells suitable for the attachment-detachment of objects according to the invention. Black=attachment and/or detachment zone, dark grey=working electrode, light grey=counterelectrode, hatched=reference electrode.

These devices are represented diagrammatically in the attached FIG. 5. In this figure, "CE", "WE", "Z" and "RE" represent, respectively, the counterelectrode, the working electrode, the attachment and/or detachment zone, and the reference electrode.

The dimensions, in the plane of representation, of the electrodes and components used for the devices fabricated in this example are given as an example for the device represented in the third diagram of FIG. 5, starting from the left:
- attachment zone (Z): diameter 300 µm;
- space between the attachment zone (Z) and the working electrode (WE), and between the working electrode and the counterelectrode (CE): constant space of approximately 70 µm;
- width of the working electrodes (WE) and counterelectrode (CE): 130 µm; and
- the reference electrode (RE) is a parallelepiped of 50×200 µm.

The other devices in this figure are represented substantially on the same scale.

Example 3

Preparation of the Attachment Zone and Functionalization of this Zone with the Probe Various preparations of various zones were realized in this example, in various trials, by means of various techniques:

A) Preparation of an Attachment Zone by Electrografting of Conductive Polymers and Functionalization with Oligonucleotides In this example, the attachment zone is prepared by electrografting of a polymer layer consisting of pyrrole and of pyrrole-oligonucleotides, according to the conditions and the protocol described in the document referenced [18].

Electropolymerization of the polymer of the two monomers results in immobilization of the oligonucleotide strand (the probe) via its pyrrole ending.

B) Preparation of an Attachment Zone by Silanization and Immobilization of Various Chemical Functions The following protocols are given for the grafting of silane carrying various functions. In these protocols, the probe is the function carried by the silane.

(i) Epoxide Function

The silanization protocol described in application WO-A-02/051856 is used:
- rehydration of the surface of the microsystem (formation of silanol functions, SiOH) in a solution containing 7 g NaOH+21 ml distilled water+28 ml ethanol for 2 hours with agitation at ambient temperature;
- thorough washing with deionized water;
- drying at 80° C. for 15 minutes;
- reaction in a mixture of 30 ml toluene+0.9 ml triethylamine+36 µl 5,6-epoxyhexyltriethoxysilane for 16 hours at 80° C.;
- rinsing with acetone; and
- crosslinking for 3 hours at 110° C.

(ii) Aldehyde Function

The silanization protocol described in application WO-A-02/051856 is used:
- rehydration of the surface of the microsystem (SiOH) in a solution containing 7 g NaOH+21 ml of distilled water+28 ml ethanol for 2 hours with agitation at ambient temperature;
- thorough washing with deionized water;
- drying at 80° C. for 15 minutes;
- reaction in a mixture of 30 ml toluene+0.9 ml triethylamine+36 µl 5,6-epoxyhexyltriethoxysilane for 16 hours at 80° C.;
- rinsing with acetone;
- crosslinking for 3 hours at 110° C.;
- acid hydrolysis in 0.2N HCl for 3 hours at ambient temperature;
- rinsing with distilled water; and
- oxidation of the surface diol functions to aldehyde functions for 1 hour at ambient temperature in a solution of $NaIO_4$ (660 mg of $NaIO_4$, 30 ml deionized water).

(iii) Halide Function

The following protocol is used:
- rehydration of the microsystem surface (SiOH) in a solution containing 7 g NaOH+21 ml of distilled water+28 ml ethanol for 2 hours with agitation at ambient temperature;
- thorough washing with deionized water;
- drying at 80° C. for 15 minutes;
- reaction in a mixture of 20 ml toluene+0.6 ml diisopropylethylamine+50 µl ((p-chloromethyl)-phenylethyl)trimethoxysilane for 24 hours at ambient temperature;
- rinsing with ethanol; and
- crosslinking for 3 hours at 110° C.

C) Preparation of an Attachment Zone by Adsorption of Polymers, of Proteins or of Thiols Carrying Chemical Functions In all cases, this involves immersing the electrode or the surface constituting the attachment zone in the solution made up with a solvent that is suitable for each type of molecule:

aqueous solution for proteins,
ethanol for thiols,
for a sufficient period of time (at ambient temperature):
1 hour for proteins,
24 hours for thiols under argon.

The methods used are described in the documents referenced [8] to [12] in the attached reference list. In all these above methods, the distilled water can be replaced with deionized water.

In these cases, the probe is either a function carried by the grafted thiols, or the protein or the polymer that has been immobilized, for example at the surface of the microsystem, so as to form the attachment zone.

Example 4

Example of Reversible "Passive" Attachment and "Active" Detachment, via the Electrochemical Process, According to the Present Invention In this example, the attachment used is as follows:
the probe ("A") is an oligonucleotide strand immobilized via polypyrrole on an attachment zone of a device according to the invention produced as in Examples 1 and 2;
the target "B" is an oligonucleotide complementary to the probe "A", and carrying a biotin;
another molecule, called "C", which is an object to be anchored via the target to the attachment zone, is a label: a streptavidin-phycoerythrin (fluorescent conjugate).

The probe attachment protocol is that described in the document referenced [18]. The oligonucleotides were modified so that they contained a pyrrole group. These modified oligonucleotides are then immobilized on the attachment zone by electrografting.

The biotinylated complementary targets (0.1 µM) were hybridized for 15 minutes at 50° C. and the object (streptavidin-phycoerythrin, commercial solution diluted 10-fold) was then immobilized on the attachment zone by chemical affinity between the biotin and the streptavidin for 5 minutes at ambient temperature.

Rinsing steps are carried out with a phosphate buffered saline (NaCl=27 mM, KCl=138 mM)+0.3% Tween.

The presence of fluorescence is characteristic of the attached state of the object "C". This fluorescence is observed under a fluorescence microscope (Provis (trade mark)).

For the electrochemical activation: the microsystem is connected to a potentiostat (AutoLab PGstat100, from the company Ecochemie) and by chronoamperometry: a potential of V=−1.2 V, relative to an Ag/AgCl reference electrode, is applied to the working electrode of the microsystem for 2 seconds.

Figure 1:
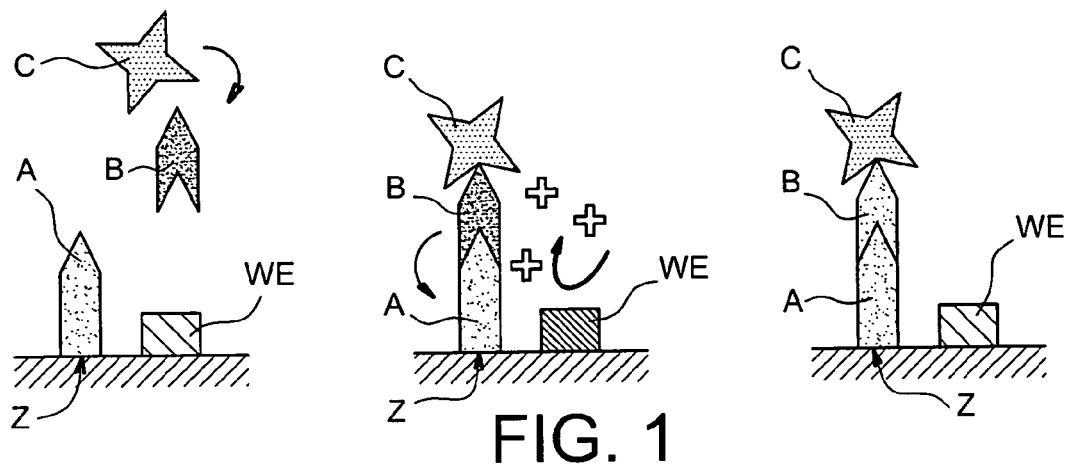
FIG. 1 represents, diagrammatically, a strategy for attachment of one or more biological and/or chemical element(s) via the electrochemical process, according to the method of the invention: on the left: the various elements are brought together (probe "A", target "B" and object "C"); in the centre: activation, via the electrochemical process, and local variation in pH (indicated by the arrow and the small positive signs) promoting assembly; on the right: the object "C" is attached, by means of the target, to the probe.
Figure 2:
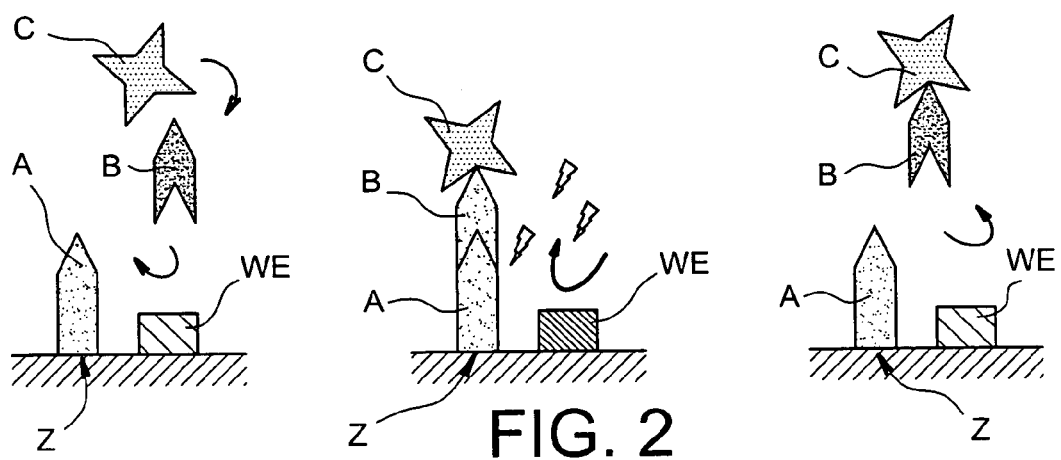
FIG. 2 represents, diagrammatically, a strategy for detachment of one or more biological and/or chemical element(s), via the electrochemical process, according to the method of the invention: on the left: assembly of the target "B" and of the object "C" on the probe "A"; in the centre; activation, via the electrochemical process, by means of the working electrode "WE" and local variation in pH (indicated by the arrow and the small lightening symbols) for the detachment; on the right: the object "C" is detached with "B" ("B-C")
Figure 3:
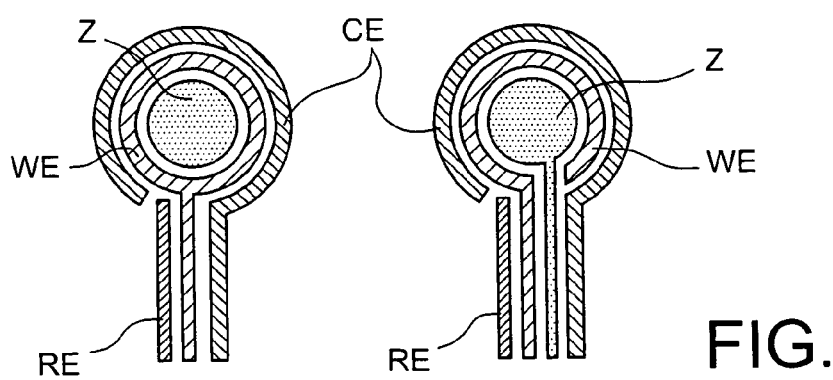
FIG. 3 represents, diagrammatically, two examples of design of a device with three or four electrodes (respectively, on the left and on the right).
Figure 4:
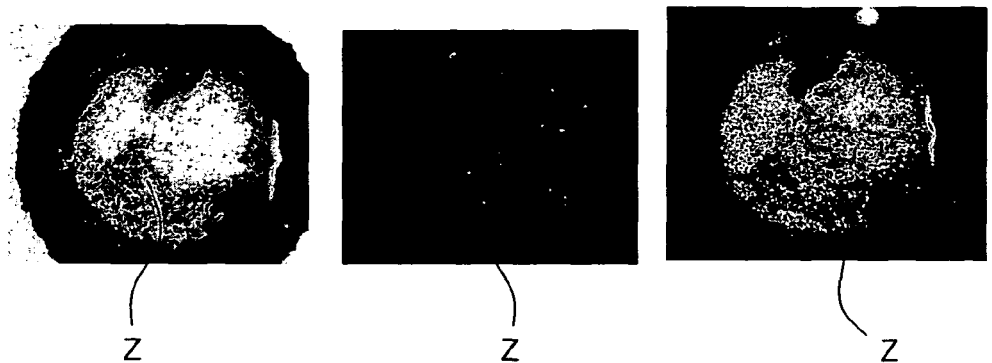
FIG. 4 represents three photographs of an attachment and detachment zone to which fluorescent objects have been attached according to the method of the present invention: immediately after attachment (photograph on the left), after electrochemical detachment (photograph in the middle) and after a further attachment (photograph on the right).

The state in which the target is anchored by the probe is confirmed by observation of the fluorescence signal, as appears in the attached FIG. 4, image on the left. The detached state is verified when the fluorescence signal disappears, as is visible in the attached FIG. 4, central image.

This electrochemical process does not affect the reversibility of the attachment, since a further attachment of fluorescent objects was carried out under the same conditions and was accompanied by the observation of a new fluorescence signal visible in FIG. 4, image on the right.

Successive attachments and detachments on the same attachment and detachment zone also showed that the process can be repeated without impairment of the functionality "A" of this attachment and detachment zone.

Example 5

Example of a Train of Electrochemical Potentials Making it Possible to Manage and Localize the Electrically Controlled Variation in pH in the Method of the Invention The choice of the electrode design and of the carrier solution, but also the choice of an appropriate train of potentials, makes it possible to control the localization of the detachment process.

For example, colorimetric and electrochemical tests carried out using concentric microelectrodes such as those fabricated in Example 2 demonstrated the possibility of localizing the phenomenon of electrochemical variation in pH precisely to the vicinity of the working electrode (active electrode).

Figure 6:
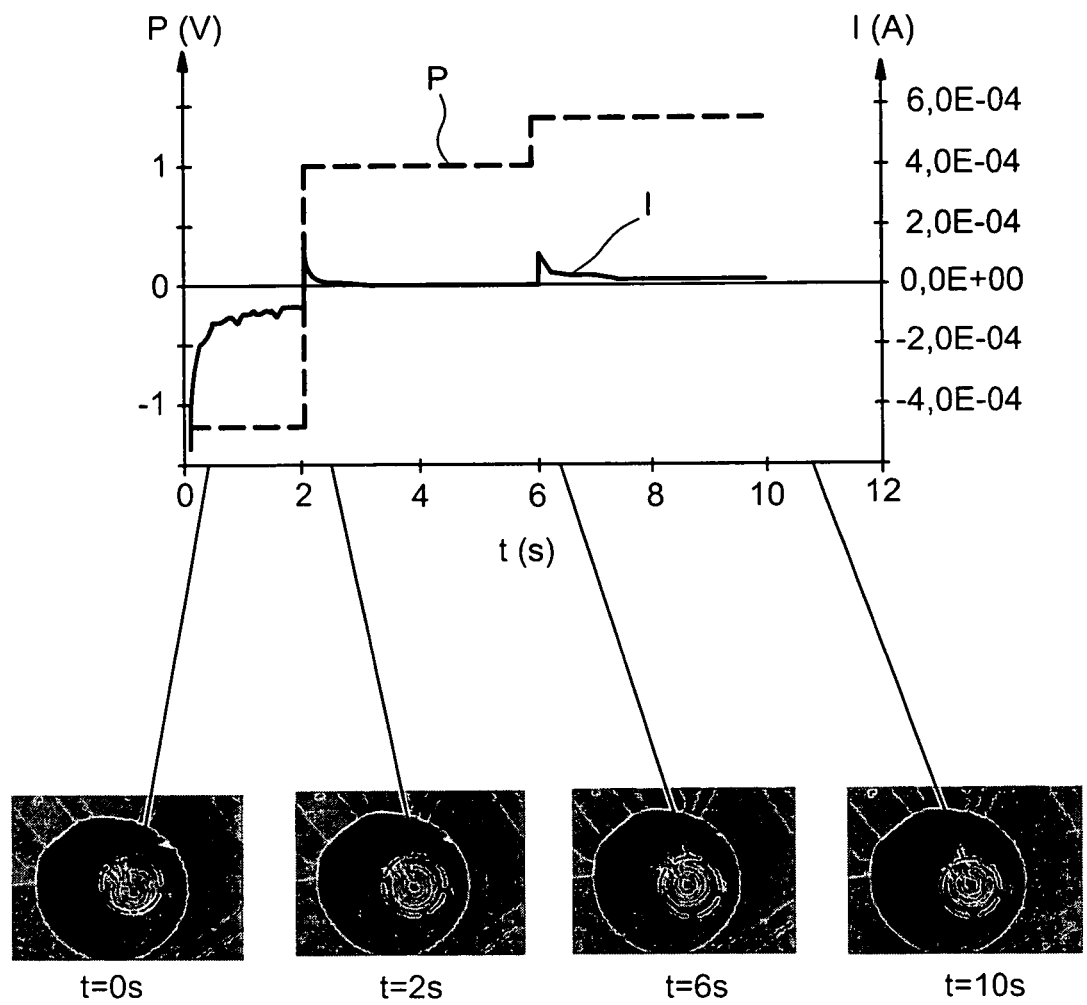
FIG. 6 represents three photographs of an electrochemical microcell according to the present invention in three different states: resting (image on the left), during the electrochemical activation (image in the middle) and after electrochemical correction of the variation in pH (image on the right). The variation in pH is demonstrated using a coloured indicator, in this case cresol red. These three photographs are shown in relation to a graph showing the application of the potential (P) (in V) and of the current (I) obtained (in A) to the working electrode as a function of time (t) (in s).

For example, a drop of aqueous solution containing a coloured indicator, for example chosen from bromocresol blue, bromocresol green, thymol blue, phenolphthalein and chlorophenol red, cresol red, or tropeolin O, changes colour only above the active electrode and above the attachment and/or detachment zone and disappears rapidly when the succession of the train of electrochemical potentials is applied, as is visible in the attached FIG. 6. The change in colour of the abovementioned indicators lies between 0.2 and 13 pH units.

Procedure:
in various trials, electrochemical microcells fabricated as in Examples 1 and 2 were covered with phosphate buffered solutions ($KH_2PO_4$ and $Na_2HPO_4$) of various pHs: 4.6, 5.1, 6.0, 7.0, 7.4, 8.0 and 9, and containing a few % of various coloured indicators: phenolphthalein, cresol red, thymol blue, bromothymol blue, bromocresol green, methyl yellow and chlorophenol red, whose ranges are between pH 0.2 and 10.

These microsystems are then connected to a potentiostat and potentials of from −0.8 V to −1.4 V and of from +0.8 V to +2.0 V are applied for 2 to 10 s.

The variations in colours are observed under white light using an optical bench composed of a binocular lens, a colour CDD camera and an image acquisition system.

Figure 7:
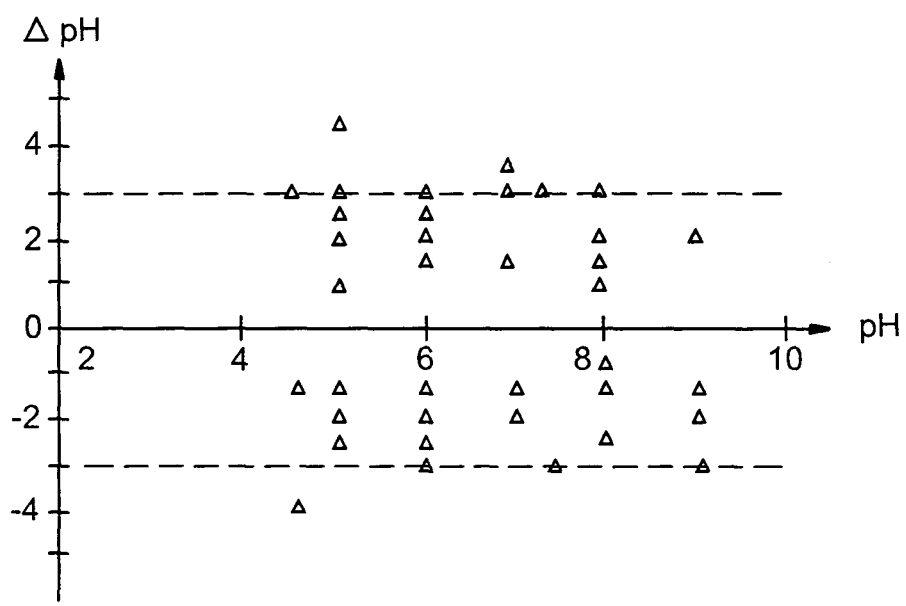
FIG. 7 is a graph representing the variation in pH ($\Delta$pH) obtained, via the electrochemical process, in the vicinity of the working electrode and of the attachment/detachment zone of a device according to the invention, as a function of the pH (initial pH) of the medium in which the device is immersed (buffer solution).

The variations in pH obtained on the working electrode (WE) and the attachment zone (Z) range up to ±3 pH units, as is represented on the graph in the attached FIG. 7.

The application of this train of potentials makes it possible to immediately compensate for the variation in pH.

Photographs of the localization of the variation in pH demonstrated by means of a coloured indicator, in this case cresol red, were taken. They demonstrate the local variation in pH, via the electrochemical process, on a concentric microcell.

The variation is clearly confined above the working electrode and above the central functionalized zone (attachment and detachment surface) in accordance with the inventor's expectations, and due to the use of the present invention.

The attached FIG. 6 is a representation of a train of potentials with 3 pulses, and of corresponding photographs of the device of the invention (before and after each pulse).

In this figure, graph I=f(t) (I in A and t, the time, in s): current obtained following the application of a train of electrochemical potentials allowing the variation in pH and compensation for said variation.

These images illustrate the compensation for the variation in pH of a drop of buffered solution (PBS, pH=7.4)+cresol red. The red colour indicates a pH above 8.8. The potential (in V) is also indicated.

Example 6

Example of Attachment via the Electrochemical Process

According to the silanization method described in patent application WO-A-02/051856, epoxide functions are grafted at the surface of microsystems according to the invention so as to form attachment zones.

The latter are then placed in the presence of a solution of phosphate+10% of glycerol containing oligonucleotides (ODNs) carrying a 5'-terminal amine function (ODN-$NH_2$). This solution forms the working solution for the purposes of the present invention.

For the attachment of ODN-$NH_2$ to the attachment zone: the reaction between the epoxide and amine functions is activated by electrochemical hydroxylation according to the method of the invention: application of a potential of −1.2 V, relative to an Ag/AgCl reference electrode, to the working electrode for 1200 s.

This protocol brings about a reaction between the amine function of the ODN-$NH_2$ and the epoxide functions of the attachment zone. The oligonucleotides are then attached to the attachment zone. This attachment is detected by measuring fluorescence: a target ODN labelled with a fluorophore (streptavidin-CY3) is hybridized and the microsystem is observed using a fluorescence microscope.

The attachment of the oligonucleotides via the electrochemical process was observed by white light image and under fluorescent light.

Example 7

Detachment of Cells Immobilized at the Surface of a Microsystem

A protein matrix was grafted, by absorption for 1 hour at ambient temperature, onto devices according to the invention so as to form attachment zones according to the invention. The latter were immersed in a cell culture medium containing HELA cells (approximately $2.76 \times 10^6$ c/ml).

After incubation for 2 hours, some cells exhibited a spread-out shape, characteristic of their immobilization on a surface.

Electrochemical detachment according to the method of the invention was carried out in a drop of PBS (pH=7.4, [NaCl]=2.7 mM and [KCl]=138 mM) with modulation of pH so as to protect the cells. The electrochemical activation is similar to that presented in Example 5.

It is observed that their shape becomes rounded, which signifies that it is gradually detaching from the surface to which said cells were adhering.

These experimental results confirm the use of the present invention for attaching and/or detaching biological objects to or from an electrochemical microsystem according to the present invention.

Example 8

Example of Attachment and Detachment of a Biotin, via the Electrochemical Process According to the method of functionalization by silanization described in Example 3B)(ii), aldehyde functions are attached to the surface and are then placed in the presence of a phosphate buffered saline solution ("PBS", pH=7.4, NaCl=27 mM, KCl=138 mM) containing biotin-amine molecules ([20 mM]) (molecule available from molecular probes).

The reaction between the aldehyde and amine functions is activated by electrochemical hydroxylation (−1.2 V, relative to an Ag/AgCl reference electrode, for 7200 s, AutoLab PGstat100, Ecochemie) in a humid chamber, and results in the creation of an imine bond. The biotin-amine assembly is then attached to the surface.

To verify the attachment, a fluorophore (streptavidin-phycoerythrin) is coupled to the biotin (placed together for 5 minutes and then rinsing with a PBS solution). The attached state is detected using a fluorescence microscope.

Cleavage of the imine function is then carried out by local electrochemical protonation of the solution in contact with the microsystem. A potential of +1.6 V, relative to an Ag/AgCl reference electrode, is applied (AutoLab PGstat100, Ecochemie) for 7200 s and, after rinsing with a buffer solution, the microsystem is observed under a fluorescence microscope.

The disappearance of the signal indicates the detachment.

Another attachment reaction is carried out, which verifies the complete reversibility and proves that the disappearance of the signal is only due to the detachment of the target, i.e. of the biotin.

Example 9

Example of Attachment and Detachment of a Target, via the Electrochemical Process In this example, an attachment zone capable of attaching a target "B" capable of "carrying" an object "C" is prepared.

The attachment zone is functionalized with an aldehyde function (probe "A"), and the target "B" is 2-hydrazinopyridine dihydrochloride carrying a hydrazine function.

According to the method of functionalization by silanization described in Example 3B)(ii), aldehyde functions are attached to the surface and are then placed in the presence of a phosphate buffer solution containing a 2-hydrazinopyridine dihydrochloride carrying a hydrazine function ([25 mg/ml]).

Electrochemical hydroxylation (−1.2 V, relative to an Ag/AgCl reference electrode, for 58 000 s, AutoLab PGstat100, Ecochemie) in a humid chamber allows the formation of a hydrazone bond, between the aldehyde and hydrazine functions (deprotection of hydrazine hydrochloride in an alkali medium).

The attachment is verified by multireflect ion infrared, where a peak characteristic of the pyridine group is detected.

Cleavage of the hydrazone function is then catalysed by local electrochemical protonation of the solution in contact with the microsystem. A potential of +1.6 V, relative to an Ag/AgCl reference electrode, is applied (AutoLab PGstat100, Ecochemie) for 22 000 s and, after rinsing with a buffer solution, the microsystem is observed.

The disappearance of the peak indicates the detachment.

Example 10

Example of Attachment and Detachment of an Object, via the Electrochemical Process The functionalization zone and the target of Example 9 are used.

A protein (object "C") is grafted onto the target, comprising an activated ester function and a protected hydrazine function (for example, succinimidyl hydraziniumnicotinate hydrochloride), and the hydrazine function is then deprotected so as to be able to be attached.

The target-object assembly is "attachable" to and "detachable" from the functionalization zone via the target, which is here used as a linker, according to the method of the present invention.

Example 11

Example of Attachment and Detachment of an Antibody

This example shows a use of the present invention with a biological molecule.

The probe attachment protocol is that described in the document referenced [18]. It involves immobilizing modified oligonucleotides (comprising a pyrrole group) by electrografting. The biotinylated complementary targets (0.1 µM) are hybridized for 15 minutes at 50° C.

Protein stacking (avidin/biotinylated protein A/antibody) is then carried out. The various steps of the stacking are carried out either in situ or in solution (PBS), and the stacking can be carried out element by element or in an overall mixture. In any case, each step is carried out by placing the elements together for 1 hour 30 minutes with agitation and at ambient temperature. The concentrations used are 1 mg/ml of avidin and protein A and 20 mg/ml of antibody (anti-*E. coli* AB). The rinsing steps are carried out with a phosphate buffered saline (PBS, pH=7.4, NaCl=27 mM, KCl=138 mM)+0.3% of Tween. To verify the attachment, a fluorescein-labelled antibody is used. The observation, under a microscope, of a fluorescence signal is characteristic of the attached state of the object.

Electrochemical detachment: the microsystem is connected to a potentiostat (AutoLab PGstat100, Ecochemie) and by chronoamperometry a potential of V=−1.2 V, relative to an Ag/AgCl reference electrode, is applied to the microsystem for 4 s.

After rinsing with a solution of PBS+0.3% Tween, the microsystem is observed under a fluorescence microscope. The disappearance of the signal indicates the detachment.

Another attachment reaction carried out verifies the complete reversibility and proves that the disappearance of the signal is only due to the detachment of the target, i.e. of the antibody and the rest of the protein stack.

Example 12

Example of Attachment of a Ferrocene

This example shows a use of the present invention with a chemical molecule.

The functionalization is carried out by grafting of an acid thiol: immersion of the surface of the microsystem in a solution of 1 mM 11-mercapto-undecanoic acid in ethanol for 24 hours under argon, and rinsing in an ultrasonic bath in ethanol for 10 minutes. An activated ester function is then synthesized by reaction between the acid function and N-hydroxysuccinimide. The acid is placed in the presence of N-hydroxysuccinimide (4 mM) and of N,N'-dicyclohexylcarbodiimide (4 mM) in chloroform for 2 hours at ambient temperature, according to the protocol of reference [21].

The surface of the microsystem then exhibits activated ester functions. The latter are subsequently placed in the presence of a phosphate buffered solution (pH 7.4) containing ferrocene-amine molecules ([20 mM]), synthesized according to the protocol described in reference [22].

Electrochemical activation catalyses the formation of an amide bond. The attachment by hydroxylation takes place under the following conditions: −1.4 V, relative to an Ag/AgCl reference electrode, for 22 000 s (AutoLab PGstat100, Ecochemie). The ferrocenes are then attached to the surface. Detection is carried out by electrochemistry (cyclic voltammetry, sweeping from 0 V to 0.5 V relative to an Ag/AgCl reference electrode, at 50 mV/s). The observation of an oxidation peak in this range of potentials is characteristic of the presence of ferrocene.

Example 13

First example of Attachment and Detachment of a Bacterium

This example shows a use of the present invention with a biological object.

The probe attachment protocol is that described in the document referenced [18]. It involves immobilizing modified oligonucleotides (containing a pyrrole group) by electrografting. The biotinylated complementary targets (0.1 µM) were hybridized for 15 minutes at 50° C. Protein stacking (avidin/biotinylated protein A/antibody+bacterium) is then carried out.

The various steps of the stacking are carried out either in situ or in solution, and the stacking can be carried out element by element or in an overall mixture. In any case, each step is carried out by placing the elements together for 1 hour 30 minutes with agitation and at ambient temperature.

The concentrations used are 1 mg/ml of avidin and protein A and 20 mg/ml of antibody (anti-*E. coli* AB). The concentration of the *E. coli* (DH5α) suspension is that of an overnight culture (inoculation of 2 ml of LB culture medium, Gibco-BRL) concentrated 15-fold. The rinsing steps are carried out with a phosphate buffered saline (PBS, pH=7.4, NaCl=27 mM, KCl=138 mM).

The presence of bacteria is observed under a microscope, under white light.

Electrochemical detachment: the microsystem is connected to a potentiostat (AutoLab PGstat100, Ecochemie) and by chronoamperometry a potential of V=−1.2 V, relative to an Ag/AgCl reference electrode, is applied to the microsystem for 4 seconds.

It was verified beforehand that these bacteria withstand these electrochemical conditions. A drop of suspension of acrydine-labelled bacteria (acrydine indicates live or dead state) was deposited on the microsystem, identical electrochemical conditions were applied, and the bacteria were observed under fluorescent light.

The latter are still alive after application of the electrochemical pH.

After rinsing with a PBS solution, the microsystem is observed under a microscope, under white light, so as to verify the absence of bacteria.

Example 14

Second Example of Attachment and Detachment of a Bacterium

The protocol applied in this example is the same as in Example 13, except that the 1st part of the protocol, up to the stacking, is carried out according to Example 8 above.

Results equivalent to those of Example 13 are observed.

Example 15

Example of Attachment of an Aminoglycan

This example shows a use of the present invention with a biological molecule of pharmacological interest.

Halide functions (Cl) are grafted at the surface of the Microsystems according to the protocol described in Example 3B)(iii).

The halides (Cl) are placed in the presence of a solution of glucosamine (100 mM). The reaction consisting of substitution of halide functions (Cl) with amine functions is activated by electrochemical hydroxylation (−1.2 V, relative to an Ag/AgCl reference electrode, for 7200 s, AutoLab PGstat100, Ecochemie).

The presence of sugar is verified by multireflection infrared, where peaks characteristic of the specific groups of sugars, which are bonds of a heterocycle (for example, C—C, C—O, C—H, O—C—OH, C—N, O—H, N—H, etc., bonds), are detected.

BIBLIOGRAPHY

[1] E. Katz & al., pH switched electrochemistry of pyrroloquinoline quinone at Au electrodes modified by functionalized monolayers, *Journal of Electroanalytical Chemistry*, 1996, 408, 107-112.
[2] M. N. Yousaf & M. Mrksich, Dynamic substrates: modulating the behaviours of attached cells, *New Technologies for life sciences*: A trends guide (Elsevier), December 2000, 28-35.
[3] J. B. Oster (Combimatric Corporation), Overlaying electrodes for electrochemical microarrays, patent number WO 02/090963 A1, Nov. 14, 2002.
[4] V. Chechik & al., Reactions and reactivity in SAMs, *Advanced Materials*, 2000, 12(16), 1161.
[5] E. Kaganer & al., Surface Plasmon Resonance Characterization of Photoswitchable Antigen-Antibody Interactions, *Langmuir*, 1999, 15(11), 3920-3923.
[6] W. E. Hennink (Universiteit van Utrecht (NL) and Stichting voor de Technische Weterschappen (NL)), LCST polymers, patent number EP 1 072 617 A1, 31 Jan. 2001.
[7] M. Yamato et al., Novel patterned cell coculture utilizing thermally responsive grafted polymer surfaces, *Journal of Biomedical Materials Research*, 2001, 55(1), 137-140.
[8] D. J. Revell & al., SA carbohydrate Ms: formation and surface selective molecular recognition, *Langmuir*, 1998, 14, 4517-4524.
[9] J. Spinke & al., Molecular recognition at SAM: optimisation of surface fictionalisation, *Journal of Chemical Physics*, 1993, 99(9), 7012-019.
[10] C. D. Tidwell & al., Endothelial cell growth and protein adsorption on terminally functionalized, SAMs of alkanethiolates on gold, *Langmuir*, 1997, 13, 3404-3413.
[11] A. E. Kaifer, Functionalised self-assembled monolayers containing preformed binding sites, *Israel Journal of Chemistry*, 1996, 36, 3899-397.
[12] B. Piro & al., A polyamide film for dopamine entrapment and delivery, *Journal of Electroanalitical Chemistry*, 2001, 499, 103-111.
[13] C. J. Stanley (Affymetric), Electrochemical denaturation of double stranded nucleic acid, U.S. Pat. No. 6,395,489 B1, May 28, 2002.
[14] J. Wang & al., On-demand electrochemical release of DNA from gold surfaces, *Bioelectrochemistry*, 2000, 52, 111-114.
[15] FR-A-2 818 287.
[16] U.S. Pat. No. 5,919,523.
[17] WO-A-02/051856.
[18] FR-A-2 103 359.
[19] J. Voldmann, et al, Microfabrication in biology and medicine; *Annu. Rev. Biomed Eng.*, 1999, 01: 401-425.
[20] Hofmann F., et al, (Infineon Technologies); Fully electronic DNA detection on a CMOS chip: device and process issues; Electron Devices Meeting; 2002. IEDM '02. *Digest. International*; 2002 Page(s): 488-491.
[21] Godillot P. & al, Synthetic Materials, 1996, 83, pp 117-123.
[22] Baueler P et al, *Adv. Mat.*, 1996, 8, 3, pp 214.

The invention claimed is:

1. A device comprising:
   a support comprising a surface comprising an attachment zone (Z) functionalized with a probe (A) capable of binding to a target (B) so as to attach it;
   a working electrode (WE) and a counterelectrode (CE) for the working electrode, placed on the support in the vicinity of the attachment zone, wherein the working electrode surrounds the attachment zone;
   an empty space separating said attachment zone and said working electrode; and
   a means for applying a given electric current or a given potential to said working electrode so as to cause, when said attachment zone and said electrodes are immersed in an aqueous solution, a local variation in pH in the region of said attachment zone.

2. The device of claim 1, wherein the counterelectrode surrounds said working electrode.

3. The device of claim 1, wherein the working electrode, the counterelectrode and the attachment zone are in a design selected from the group consisting of an interdigitated comb design, a spiral design and a concentric design.

4. The device of claim 1, wherein the means for applying a given electric current or a given potential to said working electrode are means for applying one or more given current or potential train(s) for one or more given period(s) of time.

5. The device of claim 1, further comprising a reference electrode placed so as to be able to measure the potential applied to the working electrode.

6. The device of claim 1, wherein the attachment zone is in the form of an electrode.

7. The device of claim 1, wherein the probe (A) is capable of binding, according to the pH, to the target (B) so as to attach it.

8. The device of claim 7, wherein the probe is capable of binding to the target so as to attach it by an electrophilic or nucleophilic group.

9. The device of claim 7, wherein the probe is such that it is capable of binding to the target so as to attach it by an electrophilic group selected from the group consisting of aldehyde, halide, thiocyanate, isocyanate, activated ester, carbamate and epoxide functions.

10. The device of claim 7, wherein the probe is capable of binding to the target so as to attach it by a nucleophilic group selected from the group consisting of amine, alkoxide, phenol, phenate, oxyamine and hydrazine functions.

11. The device of claim 7, wherein the probe is chosen such that it can form, in the working solution, with the target molecule so as to attach it, a bond selected from the group consisting of hydrogen, peptide, amide, sulphonamide, carboxylic acid ester, sulphonic acid ester and substituted silanoate bond.

12. The device of claim 7, wherein the attachment zone is functionalized with a probe selected from the group consisting of an oligonucleotide, a protein, an enzyme, an enzyme substrate, a hormone receptor, a hormone, an antibody, an antigen, a eukaryotic cell, a prokaryotic cell, at least one fragment of a prokaryotic cell, an alga and a microscopic fungus.

13. The device of claim 1, wherein the attachment zone and the working electrode are coplanar.

* * * * *